(12) United States Patent
Kondo et al.

(10) Patent No.: US 8,940,947 B2
(45) Date of Patent: Jan. 27, 2015

(54) GLYCERIN PURIFICATION METHOD

(71) Applicant: Hitachi, Ltd., Tokyo (JP)

(72) Inventors: Takeyuki Kondo, Ibaraki (JP);
Masayuki Kamikawa, Ibaraki (JP);
Kenichiro Oka, Ibaraki (JP); Toshiaki Matsuo, Ibaraki (JP); Masashi Tanto, Tokyo (JP); Yasunari Sase, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/138,359

(22) Filed: Dec. 23, 2013

(65) Prior Publication Data

US 2014/0114095 A1    Apr. 24, 2014

Related U.S. Application Data

(63) Continuation of application No. 13/883,776, filed as application No. PCT/JP2010/070131 on Nov. 11, 2010, now abandoned.

(51) Int. Cl.
*C07C 29/74* (2006.01)
*C07C 29/76* (2006.01)

(52) U.S. Cl.
CPC .............. *C07C 29/76* (2013.01); *C07C 29/74* (2013.01)
USPC ........................................ 568/870; 568/869

(58) Field of Classification Search
CPC ................................. C07C 29/74; C07C 29/76
USPC .................................................. 568/869, 870
See application file for complete search history.

(56) References Cited

FOREIGN PATENT DOCUMENTS

| JP | 58-126827 | 7/1983 |
|---|---|---|
| JP | 58-144333 | 8/1983 |
| JP | 6-184024 | 7/1994 |
| JP | 7-197047 | 8/1995 |
| WO | WO 2009/136181 A1 | 11/2009 |

OTHER PUBLICATIONS

Kentaro Shima, Production, Application and Economic Performance of 1,3-PDO and PTT), CMC Publishing Co., Ltd. Planet Division, Aug. 2000.
Masaru Watanabe et al, Acrolein synthesis from glycerol in hot-compressed water, Bioresource Technology 98 (2007), pp. 1285-1290.

*Primary Examiner* — Elvis O Price
(74) *Attorney, Agent, or Firm* — Antonelli, Terry, Stout & Kraus, LLP.

(57) ABSTRACT

This invention provides a cost-effective method for removing impurities from waste glycerin generated in the process of biodiesel production, so as to prevent a supercritical water reaction tube from clogging, when synthesizing acrolein by allowing supercritical water and acid to react with glycerin. The method for purification of glycerin of the invention comprises steps of: heating glycerin containing alkali metal, alcohol, organic fatty acid, and water under reduced pressure, so as to remove alcohol and water; adding sulfuric acid to glycerin from which alcohol and water have been removed, so as to neutralize glycerin; subjecting neutralized glycerin to centrifugation, so as to separate and remove a sulfate of alkali metal and organic fatty acid; adding a sulfate of alkaline earth metal to glycerin collected via centrifugation; and subjecting a mixture of glycerin and a sulfate of alkaline earth metal to centrifugation, so as to separate and remove a sulfate of alkali metal and an alkaline earth metal salt of organic fatty acid.

6 Claims, 8 Drawing Sheets

GLYCERIN PURIFICATION METHOD

CROSS-REFERENCE TO RELATED APPLICATION

This application is a continuation application of U.S. application Ser. No. 13/883,776, filed May 7, 2013, the contents of which are incorporated herein by reference.

TECHNICAL FIELD

The present invention relates to a method for purification of a glycerin waste product obtained, as a by-product, in the process for biodiesel production. More particularly, the present invention relates to a method for purification of glycerin, which is a starting material used in a process for synthesizing acrolein as a raw material of 1,3-propanediol via supercritical water treatment.

BACKGROUND ART 1,3-Propanediol is a raw material of high-quality polyester fibers, including polytrimethylene terephthalate, and the demand therefor has thus been increasing in recent years. An example of a method for synthesis of 1,3-propanediol is a method of hydration and hydrogenation of acrolein described in Non-Patent Document 1. This method involves air oxidation of propylene, which is a petroleum raw material, in the presence of a catalyst and hydration and hydrogenation of acrolein resulting therefrom. This technique has been established as an industrial production method. However, development of a method for synthesizing 1,3-propanediol from biomaterials has been desired because of an increase in crude oil prices in recent years.

The present inventors have been conducting research aimed at development of a process for synthesizing acrolein, which is a precursor for 1,3-propanediol, from a glycerin waste product obtained, as a by-product, in the process for biodiesel production.

As described in Patent Document 1, a biodiesel is generally produced by a method involving the use of an alkaline catalyst. According to this method, a triglyceride (e.g., rape-seed oil) is subjected to transesterification in the presence of an alkaline catalyst (e.g., potassium methoxide) to produce a biodiesel. As a result of such reaction, a glycerin molecule is generated from a triglyceride molecule. Because of the inclusion of an alkaline catalyst in glycerin, no cost-effective process for recycling is available. At present, accordingly, most manufacturing facilities are required to incur incineration disposal waste costs.

Meanwhile, Non-Patent Document 2 describes a method for synthesizing acrolein from glycerin with the use of supercritical water. According to this method, an aqueous solution of glycerin as a biomaterial is mixed with high-temperature supercritical water at 35 MPa, the solution is instantaneously heated to 400° C., and acrolein is then synthesized. This method is characterized in that protons of a sulfuric acid, which was added in a trace amount to an aqueous solution of glycerin, function as catalysts that accelerate the dehydration of glycerin. If a glycerin waste product generated in the process of biodiesel production is directly treated with supercritical water, however, pipe clogging may disadvantageously occur. This may occur because an alkaline catalyst contained in a glycerin waste product is precipitated in supercritical water with low permittivity. This necessitates the removal of alkali metals from glycerin obtained, as a by-product, in the process of biodiesel production.

Patent Document 2 describes a method for purification of glycerin involving ion exchange. According to this method, a glycerin waste product containing impurities such as organic fatty acid and alkali generated in the process of biodiesel production is allowed to pass through ion-exchange resin to remove such impurities, and glycerin is thus purified. The glycerin waste product contains alkali metals in an amount of approximately 4% by weight and organic fatty acids in an amount of approximately 10% by weight or more, in terms of ion concentration. When the glycerin waste product is treated without pretreatment, accordingly, the time until the ion-exchange resin reaches the breakthrough point is shortened, recycling frequency is increased, and, in turn, costs for purification are increased disadvantageously.

Patent Document 3 describes a method for purification of glycerin involving distillation (FIG. 1). According to this method, glycerin generated at the time of transesterification of fats with methanol in the presence of an alkaline catalyst is purified. This process is characterized in that hydrochloric acid is added to an alkali-containing glycerin solution to precipitate an alkali metal chloride, and the chloride is roughly separated via filtration, and the product is then purified via distillation. Since this process involves purification via distillation, a large quantity of energy is required to reheat raw materials, which leads to an increase in costs for glycerin purification.

PRIOR ART DOCUMENTS

Non-Patent Documents

Non-Patent Document 1: Kentaro Shima, 1,3-*PDO, PTT no seizo youto oyobi keizaisei* (Production, Application, and Economic Performance of 1,3-PDO and PTT), CMC Publishing Co., Ltd., Planet Division, August 2000

Non-Patent Document 2: Masaru Watanabe et al., Acrolein synthesis from glycerol in hot-compressed water, Bioresource Technology 98, 1285-1290, 2007

Patent Documents

Patent Document 1: JP Patent Publication (Kokai) No. H07-197047 A

Patent Document 2: JP Patent Publication (Kokai) No. S58-144333 A

Patent Document 3: JP Patent Publication (Kokai) No. H06-184024 A

SUMMARY OF THE INVENTION

Object to be Attained by the Invention

It is an object of the present invention to provide a cost-effective method for removing impurities from waste glycerin generated in the process of biodiesel production, so as to prevent a pipe used for supercritical water treatment from clogging, when synthesizing acrolein by allowing supercritical water and acid to react with glycerin.

Means for Attaining the Object

The present inventors discovered that the above object could be attained by neutralizing a glycerin waste product containing alkali metals and other materials with sulfuric acid and then adding a sulfate of alkaline earth metal, thereby completing the present invention. Specifically, the present invention is summarized as follows.

(1) A method for purification of glycerin comprising steps of: heating glycerin containing an alkali metal, an alcohol, an organic fatty acid, and water under reduced pressure, so as to remove the alcohol and water; adding sulfuric acid to glycerin from which the alcohol and water have been removed, so as to neutralize glycerin; subjecting neutralized glycerin to centrifugation, so as to separate and remove a sulfate of alkali metal and the organic fatty acid; adding and mixing a sulfate of alkaline earth metal to glycerin collected via centrifugation; and subjecting a mixture of glycerin with the sulfate of alkaline earth metal to centrifugation, so as to separate and remove the sulfate of alkali metal and an alkaline earth metal salt of organic fatty acid.

(2) A method for purification of glycerin comprising allowing glycerin obtained by the method for purification according to (1) to pass through cation-exchange resin, so as to separate and remove the alkali metal.

(3) A method for purification of glycerin comprising allowing glycerin obtained by the method for purification according to (2) to pass through anion-exchange resin, so as to separate and remove impurities.

(4) The method for purification of glycerin according to any of (1) to (3), wherein the sulfate of alkaline earth metal is magnesium sulfate.

Effects of the Invention

According to the present invention, an alkali metal catalyst can be separated and removed more efficiently because of a process of neutralization with sulfuric acid, following the removal of an alcohol and water from glycerin, for the following reasons. That is, a sulfate of alkali metal is generated when an alkali metal is neutralized with sulfuric acid. While a sulfate of alkali metal is highly soluble in an alcohol and in water, solubility thereof in glycerin is low. Since the efficiency for removal of an alkali metal catalyst is improved, operation costs can be reduced.

In addition, corrosion of supercritical water pipes can be reduced because of the neutralization of glycerin with sulfuric acid. Synthesis of acrolein from glycerin with the use of supercritical water is carried out with the use of sulfuric acid as a catalyst. Accordingly, glycerin may be neutralized with sulfuric acid, which is the same substance as the catalyst, so that anions existing in supercritical water can be limited to sulfate ions. Thus, the corrosion of piping materials can be reduced.

In addition, centrifugation is carried out after an alkaline earth metal is added to crude glycerin. Thus, alkali metal concentration in purified glycerin can be reduced. Since an alkaline earth metal ion has a smaller ionic radius and a higher electric charge than an alkali metal ion, an alkaline earth metal is highly likely to take an anion from an alkali metal salt. Thus, an alkali metal salt of organic fatty acid contained in crude glycerin may be allowed to react with a sulfate of alkaline earth metal also contained therein, so that an alkaline earth metal salt of organic fatty acid and a sulfate of alkali metal are generated. In general, the alkaline earth metal salt of higher fatty acid and the sulfate of alkali metal generated are precipitated due to low solubility in glycerin. Since alkali metal concentration in crude glycerin can be reduced, a supercritical water pipe can be prevented from clogging. Further, alkali metal concentration in glycerin can be reduced with the use of a sulfate of alkaline earth metal in a cost-effective manner, and purification costs can thus be reduced.

Since glycerin is purified via ion exchange, following neutralization with sulfuric acid and desalting with a sulfate of alkaline earth metal, the amount of ions adsorbing to ion-exchange resin can be reduced, and recycling frequency of ion-exchange resin and purification costs can be reduced. Further, alkali metal salts and alkaline earth metal salts of lower fatty acids, such as formic acid, acetic acid, and propionic acid, are soluble in glycerin. Accordingly, such salts cannot be separated from glycerin via neutralization with sulfuric acid and desalting with the addition of an alkaline earth metal salt described above. Such salts of lower fatty acids, which could not be separated and removed, can be assuredly removed with the use of ion-exchange resin. This can prevent a supercritical water pipe from clogging, which in turn can improve stability of plant operation and reduce operation costs.

EMBODIMENTS FOR CARRYING OUT THE INVENTION

Hereafter, a process of generating, as a by-product, a glycerin waste product when producing a biodiesel from fats, a process of purifying a glycerin waste product generated as a by-product, and a process of synthesizing acrolein, which is a precursor for 1,3-PDO, from purified glycerin with the use of supercritical water, are described with reference to the drawings.

Figure 1:
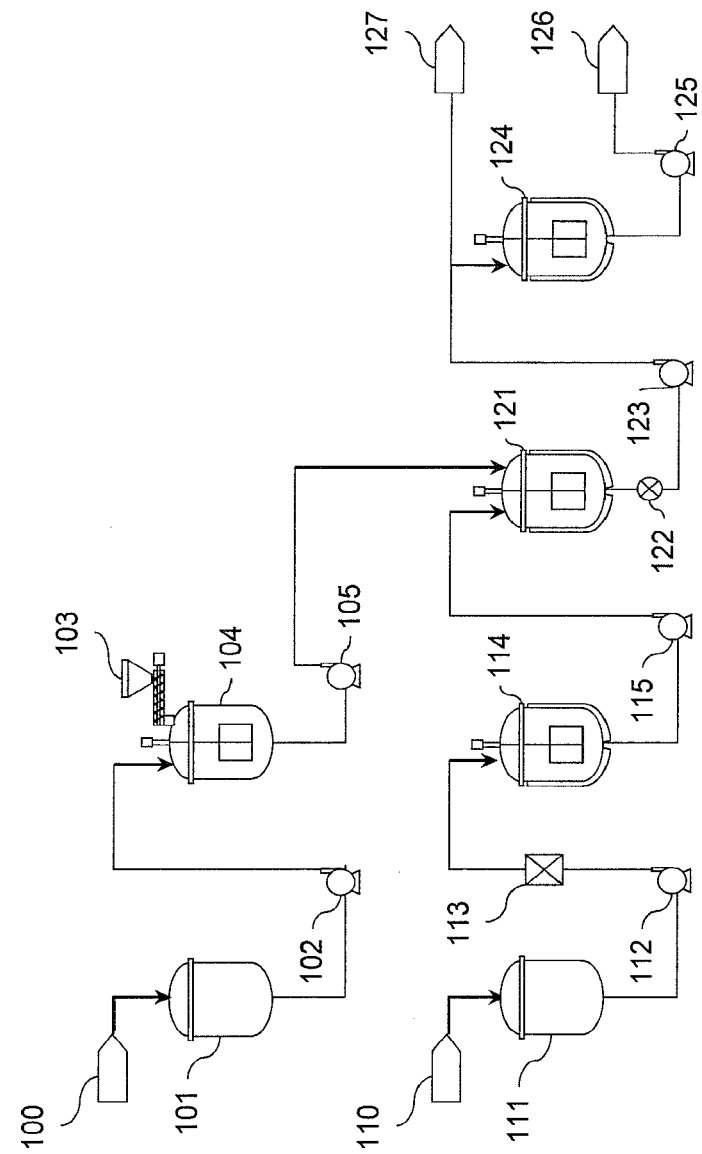
FIG. 1 shows a process for biodiesel production.

FIG. 1 shows steps of the process for biodiesel production associated with glycerin produced as a by-product. At the outset, fats are transferred from a fat header 110 to a fat tank 111 and stored therein. Examples of fats used herein include, but are not limited to, fats derived from plants, such as rapeseed, soybean, and Jatropha, animal fats, and waste cooking oils. Such fats are allowed to pass through a fat filter 113 with the aid of a fat pump 112 to remove solid components, the resultant is dehydrated via vacuum heating in a fat receiver tank 114, and the resultant is then transferred to a transesterification tank 121 with the aid of a fat pump 115.

Methanol is transferred from a methanol header 100 to a methanol tank 101 and stored therein. Ethanol may be used as an alternative to methanol. Methanol is transferred to a potassium methoxide production tank 104 with the aid of a methanol pump 102. Subsequently, potassium hydroxide is supplied to the potassium methoxide production tank 104 with the use of a potassium hydroxide feeder 103. Sodium hydroxide may be supplied as an alternative to potassium hydroxide.

Methanol is mixed with potassium hydroxide in the potassium methoxide production tank 104 at room temperature, and methanol containing potassium methoxide is then generated. The amount of potassium hydroxide or sodium hydroxide to be added relative to 1 $m^3$ of methanol is preferably about 37.3 kg or 26.6 kg. Methanol containing potassium methoxide is transferred to a transesterification tank 121 with the aid of a potassium methoxide pump 105.

In the transesterification tank 121, fats and methanol containing potassium methoxide are agitated at about 50° C. for about 3 hours. Thus, the transesterification reaction represented by chemical formula (1) proceeds, and glycerin is generated as a by-product at the time of biodiesel production. Since the reaction represented by chemical formula (1) is a static reaction, in general, the transesterification reaction is carried out by adding methanol containing potassium methoxide in two separate instances. At first, 0.1 m$^3$ of methanol containing potassium methoxide is added relative to 1 m$^3$ of fats. After the reaction has been allowed to proceed at about 50° C. for 3 hours, the reaction product is allowed to stand for 30 minutes, and the reaction product is divided into a biodiesel layer as an upper layer and a glycerin waste product layer as a lower layer. The glycerin waste product as the lower layer is selectively transferred to the subsequent process of glycerin purification. The boundary between the glycerin waste product layer and the biodiesel layer is detected with the use of a conductivity meter 122 located at the bottom of the tank. More specifically, while the biodiesel layer is low in conductivity, the glycerin waste product layer contains water and alkali metal ions, and the glycerin waste product layer thus exhibits high conductivity. Accordingly, conductivity of a liquid discharged from the tank is assayed, and a position indicating a lowering in conductivity is then detected as the boundary between the glycerin waste product layer and the biodiesel layer.

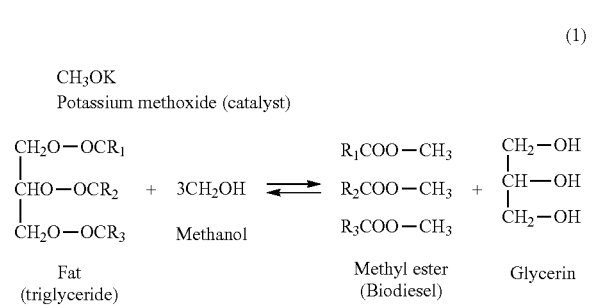

(1)

When the glycerin waste product layer is discharged from the transesterification tank 121 and the static reaction represented by chemical formula (1) proceeds to the step shown in the right side, the second transesterification reaction then takes place. Methanol containing an amount of potassium methoxide that is half of the amount of methanol added in the first process is added to the remaining biodiesel layer, and the resultant is agitated at 50° C. for 1 hour to carry out the transesterification reaction. Thereafter, the reaction solution is allowed to stand for 30 minutes, and the resultant is separated into a biodiesel layer and a glycerin waste product layer again. Thereafter, the glycerin waste product layer as the lower layer is selectively subjected to the process 127 of glycerin purification. The biodiesel remaining in the transesterification tank 121 is transferred to a pre-purification BDF tank 124 and stored therein. Thereafter, a purified biodiesel is obtained through neutralization, washing, and dehydration, although the details of the process for biodiesel purification are omitted.

While the process for biodiesel production involving the use of potassium hydroxide as a catalyst was explained, a biodiesel can be produced with the use of sodium hydroxide as an alternative to potassium hydroxide. However, use of potassium hydroxide is preferable for the following 3 reasons. For one reason, a glycerin waste product containing sodium is solid at room temperature. When it is transferred with the aid of a pump, accordingly, it is necessary that the solid be liquefied via heating at 60° C. or higher. The second reason is that, when potassium hydroxide is used, the amount of alkali remaining in a biodiesel is smaller than that when sodium hydroxide is used, and the amount of water used for washing and desalting in the process of biodiesel purification can thus be reduced. For the third reason, the solubility of a potassium compound in glycerin is lower than that of a sodium compound. With the use of potassium hydroxide, accordingly, desalting of glycerin can be more easily carried out. Table 1 and Table 2 show the solubility of potassium salt and sodium salt in glycerin.

TABLE 1

Solubility of potassium salt in glycerin and in water

| | Solubility in solvent (wt %, 20° C.) | | |
|---|---|---|---|
| Solvent | KOH | K$_2$SO$_4$ | KCl |
| Water | 52.8 | 10.0 | 25.3 |
| Glycerin | 7.6 | <0.1 (insoluble) | 3.5 |

TABLE 2

Solubility of sodium salt in glycerin and in water

| | Solubility in solvent (wt %, 20° C.) | | |
|---|---|---|---|
| Solvent | NaOH | Na$_2$SO$_4$ | NaCl |
| Water | 52.2 | 16.0 | 26.4 |
| Glycerin | 15.1 | 8.1 | 8.1 |

Figure 2:
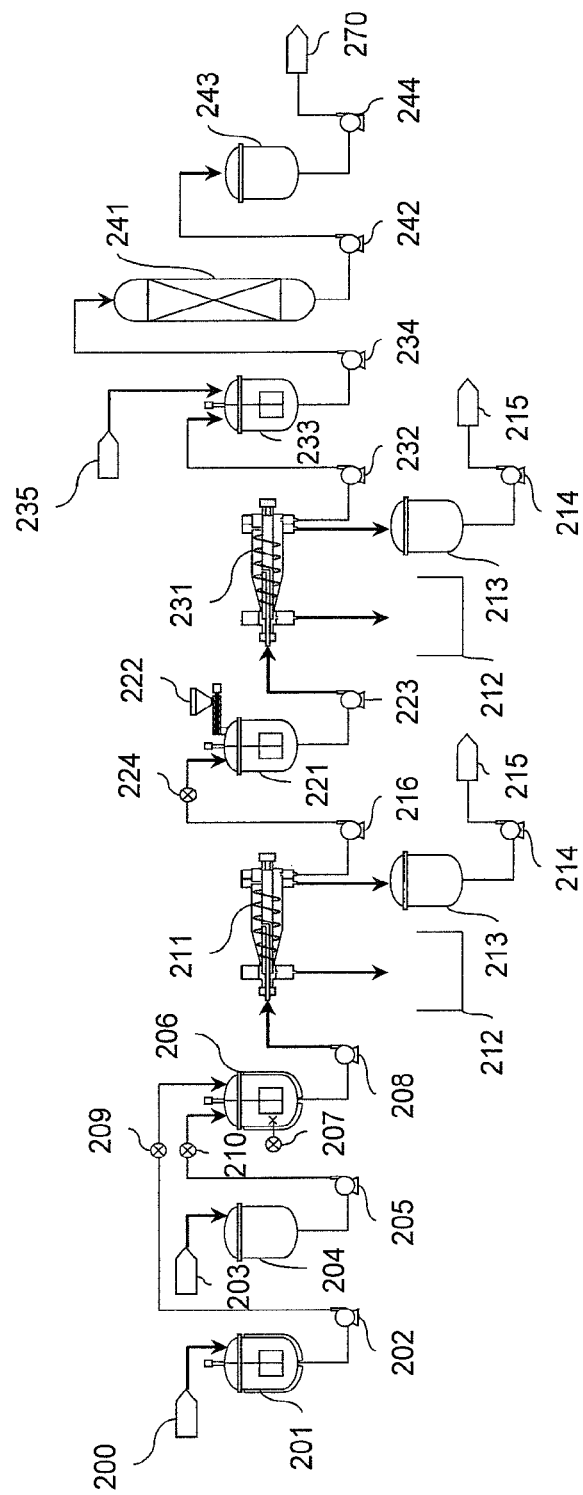
FIG. 2 shows a process for purification of a glycerin waste product.

Subsequently, a process for purification of a glycerin waste product is described with reference to FIG. 2. The glycerin waste product is stored in a waste glycerin tank 201 and then transferred to a neutralization tank 206 with the aid of a waste glycerin pump 202. The amount of the glycerin waste product is measured with the use of a waste glycerin integrating flow meter 209. The pH level of glycerin is measured in the neutralization tank. The glycerin waste product is in a liquid state at room temperature when potassium methoxide is used as a catalyst for biodiesel production; however, it is in a solid state at room temperature when sodium methoxide is used. When sodium methoxide is used, accordingly, it is necessary for the waste glycerin tank 201 and the neutralization tank 206 to be heated to 60° C. or higher and for agitation to be carried out.

Concentrated sulfuric acid that neutralizes potassium-containing glycerin is transferred from the sulfuric acid tank 204 to the neutralization tank 206 with the aid of the sulfuric acid pump 205. If hydrogen ion concentration determined with the pH meter 207 in the waste glycerin tank is designated as [H$^+$] (mol/l) and the amount of the transferred glycerin waste product determined with the use of the glycerin waste product integrating flow meter is designated as V (1), it is preferable that the amount of sulfuric acid to be transferred be adjusted to a level represented by [H$^+$]×V/2 (mol). At the time of neutralization, the temperature of the jacket of the neutralization tank 206 is adjusted to 80° C. with agitation, the air in the tank is evacuated, and water and methanol are allowed to evaporate. By conducting evacuation at the time of neutralization, the neutralization energy can be utilized for heating of the reaction solution. Thus, purification costs can be reduced. The pH level of glycerin is changed from 6 to 8 as a result of the neutralization step.

As described above, glycerin is neutralized with the aid of sulfuric acid after an alcohol and water have been removed therefrom. Thus, the efficiency for separation and removal of an alkali metal catalyst can be improved. This can be realized because a sulfate of alkali metal is generated when neutralizing an alkali metal with sulfuric acid; however, a sulfate of alkali metal exhibits high solubility in an alcohol and in water but low solubility in glycerin (see Table 1 and Table 2 above). Since the efficiency for removal of an alkali metal catalyst is improved, purification costs can be reduced.

Synthesis of acrolein from glycerin with the use of supercritical water is carried out with the use of sulfuric acid as a catalyst. Accordingly, glycerin may be neutralized with sulfuric acid, which is the same substance as the catalyst, so that the anions existing in supercritical water can be limited to sulfate ions. Thus, corrosion of piping materials can be reduced.

The neutralized glycerin waste product is transferred to a continuous centrifuge 211 with the aid of a neutralizer pump 208. In the continuous centrifuge 211, a glycerin waste product is transferred into the rotating conical tube, and the waste is separated into potassium sulfate, crude glycerin, and organic fatty acid from the outermost layer. Potassium sulfate is scraped therefrom with a screw rotating at a speed different from that of the conical tube and discharged to the outside of the equipment. In contrast, crude glycerin and organic fatty acid are separately discharged from two outlets located at different distances from the rotary axis. After potassium sulfate has been discharged to a potassium sulfate pit 212, it is washed with acetone and used as a raw material for a potassium fertilizer and alum. After organic fatty acid has been discharged to an organic fatty acid tank 213, it is subjected to the process 215 of organic fatty acid treatment, and it is then converted into a biodiesel via transesterification. The flow rate of crude glycerin is integrated with the use of a crude glycerin flow meter 224 and the crude glycerin is then transferred to a magnesium sulfate mixing tank 221. While FIG. 2 shows an embodiment involving the use of a continuous centrifuge, the waste may be allowed to stand in the neutralization tank 206 for 3 hours to separate the waste into potassium sulfate, crude glycerin, and organic fatty acid from the lowermost layer. Alternatively, the neutralized glycerin waste product may be filtered through a filter. In such a case, it is preferable that the pore diameter of the filter be 1 μm or less.

Crude glycerin from which potassium sulfate and organic fatty acid have been removed in a simple manner is transferred to a magnesium sulfate mixing tank 221. Magnesium sulfate is added with the aid of a magnesium sulfate screw feeder 222 in the tank, and magnesium sulfate is mixed with crude glycerin at 90° C. for 3 hours. It is preferable that the amount of magnesium sulfate added be approximately equivalent to the organic fatty acid content, which is determined by sampling crude glycerin and measuring the organic fatty acid content. When the amount of organic fatty acid cannot be measured, the amount of magnesium sulfate added is preferably about 1% by weight relative to the weight of crude glycerin. By mixing magnesium sulfate with crude glycerin, a potassium salt of organic fatty acid in crude glycerin is converted into a magnesium salt of organic fatty acid exhibiting low solubility in glycerin. Thus, magnesium of organic fatty acid is precipitated from glycerin. As a result of removal of potassium of organic fatty acid that has enhanced the solubility of the potassium component, the solubility of potassium is lowered, and potassium sulfate is further separated and removed.

Since centrifugation is carried out after an alkaline earth metal has been added to crude glycerin, alkali metal concentration in purified glycerin can be reduced. An alkaline earth metal ion has a smaller ionic radius and a higher electric charge than an alkali metal ion. Accordingly, an alkaline earth metal is highly likely to take an anion from an alkali metal salt. Thus, an alkali metal salt of organic fatty acid contained in crude glycerin may be allowed to react with a sulfate of alkaline earth metal also contained therein, so that an alkaline earth metal salt of organic fatty acid and a sulfate of alkali metal are generated. In general, the alkaline earth metal salt of higher fatty acid and the sulfate of alkali metal generated are precipitated due to low solubility in glycerin. Thus, alkali metal concentration in crude glycerin can be reduced. This can prevent a supercritical water pipe from clogging. In addition, alkali metal concentration in glycerin can be reduced with the use of an inexpensive sulfate of alkaline earth metal. Thus, purification costs can be further reduced.

Crude glycerin mixed with magnesium sulfate is transferred to a continuous centrifuge 231 with the aid of a mixture transfer pump 223, and it is then separated into potassium sulfate, simply purified glycerin, and organic fatty acid. The constitution of the continuous centrifuge 231 is the same as that of the continuous centrifuge 211. Potassium sulfate is discharged to a potassium sulfate pit 212, organic fatty acid is stored in an organic fatty acid tank 213, it is subjected to the process 215 of organic fatty acid treatment 215, and transesterification is carried out in the presence of sulfuric acid and methanol to convert potassium sulfate into a biodiesel. While FIG. 2 shows an embodiment involving the use of a continuous centrifuge, the waste may be allowed to stand in a magnesium sulfate mixing tank 221 for 3 hours, to separate the waste into potassium sulfate, simply purified glycerin, and organic fatty acid from the lowermost layer. Alternatively, crude glycerin to which magnesium sulfate has been added may be filtered through a filter. In such a case, it is preferable that the pore diameter of the filter be 1 μm or less.

Glycerin purified with the continuous centrifuge 231 in a simple manner is stored in a purified glycerin tank 233, it is transferred to a cation exchange tower 241, and trace amounts of potassium that could not be completely removed via centrifugation described above are separated and removed via ion exchange. Since purified glycerin is subjected to ion exchange, following neutralization with sulfuric acid and desalting with a sulfate of alkaline earth metal, the amounts of ions adsorbing to ion-exchange resin can be reduced, and recycling frequency of ion-exchange resin and purification costs can be reduced. Further, alkali metal salts and alkaline earth metal salts of lower fatty acids, such as formic acid, acetic acid, and propionic acid, are soluble in glycerin. Accordingly, such salts cannot be separated from glycerin via neutralization with sulfuric acid and desalting with the addition of an alkaline earth metal salt described above. Such salts of lower fatty acids, which could not be separated and removed, can be assuredly removed with the use of ion-exchange resin. This can prevent a supercritical water pipe from clogging, which in turn can improve the stability of plant operation and reduce operation costs.

Ion-exchanged glycerin is stored in a cation-exchanged glycerin tank 243, and it is then subjected to the process 270 of supercritical water treatment.

Subsequently, a process for synthesis of acrolein from purified glycerin via supercritical water treatment is described with reference to FIG. 3. At the outset, purified glycerin, concentrated sulfuric acid, and water are transferred from relevant headers (i.e., a purified glycerin header 320, a sulfuric acid header 321, and a water header 322) to a raw material tank 323, and the concentrations of these components are adjusted to given levels via mixing with agitation. The raw materials are transferred with the aid of a raw material high-pressure pump 325 at 35 MPa and heated to 250° C. with a raw material pre-heater 326. Ultrapure water stored in a water tank 311 is transferred with a supercritical water high-pressure pump 312 at 35 MPa and heated to 500° C. with a supercritical water pre-heater 313. These components are mixed at a juncture 327, the mixture is adjusted to 400° C. and 35 MPa instantaneously, and the reaction is then initiated. Since potassium sulfate concentration and sodium sulfate concentration that would not cause pipe clogging under the conditions for supercritical water treatment (i.e., 400° C., 35 MPa) are 0.04% by weight and 0.06% by weight, respectively, it is necessary to remove salts to a level equivalent to or lower than such concentration.

It is preferable that glycerin concentration immediately after mixing of raw materials with supercritical water be 15% by weight to 30% by weight. By adjusting the initial glycerin concentration to 15% by weight or higher in the reaction solution, the costs required for heating and pressurization of supercritical water can be reduced, and the process for synthesis of acrolein from a petroleum raw material can be made cost competitive. When the initial glycerin concentration is adjusted to 30% by weight or higher in the reaction solution, a secondary reaction that generates formaldehyde and acetaldehyde becomes dominant as shown in Chemical Formula (2), the reaction efficiency is lowered, and costs for acrolein production may occasionally be increased for the following reasons. When glycerin concentration is low and a sufficient quantity of coordinated water is present in the vicinity of glycerin, in general, hydrogen ions are highly active, protons are added to secondary hydroxyl groups of glycerin, and the acrolein synthesis reaction proceeds through the two-step dehydration reaction. When glycerin concentration is high and the quantity of coordinated water that contributes to the reaction is decreased, however, dehydration proceeds at the terminal hydroxyl group, and the main reaction becomes non-dominant.

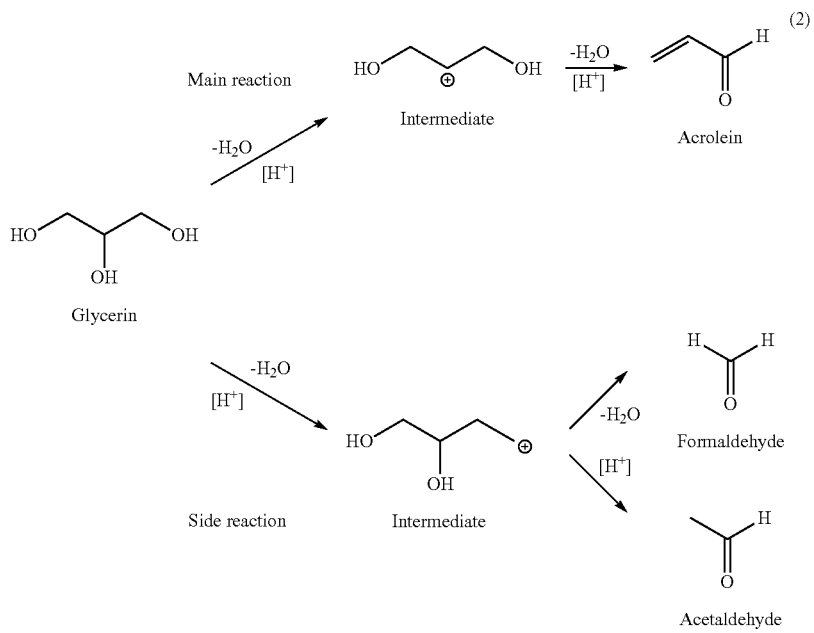

(2)

In addition, proton concentration in the reaction solution may be adjusted within the range defined by formula (a), so that the reaction yield can be enhanced to 70% or higher. In formulae used herein, [H+] represents proton concentration (mM) in the reaction solution resulting from the addition of sulfuric acid, and [G] represents glycerin concentration (wt %).

$$5 \times \sqrt{[G]} < [H^+] < 20 \times \sqrt{[G]} \qquad (a)$$

An enhanced reaction yield leads to a reduction in the amount of by-products generated. Accordingly, it is very effective for prevention of pipe clogging or abrasion of equipment.

The reaction time (t) may be adjusted within the range defined by formula (b) with the use of glycerin concentration [G] (wt %) in the reaction solution, so that the reaction yield can be enhanced.

$$\frac{15}{[G]} < t < \frac{60}{[G]} \qquad (b)$$

In order to improve the efficiency for mixing supercritical water with raw materials, a plurality of swirl flow mixers described in JP Patent Publication (Kokai) No. 2010-46634 A are aligned at the juncture 327 of supercritical water and raw materials, and mixing is carried out in that state. Thus, the reaction yield can be enhanced.

After the elapse of the optimal reaction time, subsequently, cooling water is transferred from the cooling water tank 341 shown in FIG. 3 to the juncture 343 of the reaction solution and the cooling water with the use of the cooling water high-pressure pump 342, and the reaction is terminated via direct mixing with cooling water. In order to terminate the reaction, it is necessary that the reaction solution be cooled to 300° C. or lower, and preferably to 250° C. The optimal duration of this reaction is determined on the second time scale, and the inner diameter of the pipe in the actual equipment is as thick as about 10 cm. In comparison with indirect cooling with the use of a double-pipe cooler, accordingly, the reaction duration can be regulated more sufficiently according to a method in which raw materials are directly mixed with cooling water. Such method is very effective for reduction of the amounts of by-products generated.

Impurities are removed from potassium-containing glycerin via neutralization with the aid of sulfuric acid and mixing with magnesium sulfate. This can prevent corrosion of a pipe occurring in the process of supercritical water treatment. That is, synthesis of acrolein from glycerin with the use of supercritical water involves the use of sulfuric acid as a catalyst. Accordingly, glycerin may be neutralized with sulfuric acid, which is the same substance as the catalyst, so that anions existing in supercritical water can be limited to sulfate ions. Thus, corrosion of piping materials can be reduced.

After the termination of the reaction, the reaction solution is allowed to pass through the filters 351a and 351b to separate coal-tar from carbon particles, carbon particles are selectively captured with the filter, and coal-tar is allowed to pass through the filter while maintaining a high viscosity. Thus, pipe clogging caused by aggregation of coal-tar and carbon particles can be prevented. In order to prevent clogging of the filters with coal-tar, it is necessary that the reaction solution be maintained at 100° C. or higher, and preferably at 250° C., after mixing with cooling water. The method of filtering the reaction solution after cooling so as to remove impurities is very effective for slowing down the speed of filter corrosion. Since pore diameters of carbon particles generated by the reaction are between 40 μm and 2 mm, filter pore diameters may be adjusted to 40 μm or less, so that the efficiency for separation and removal of carbon particles can be improved.

By preparing two or more types of filters for separation and removal of carbon particles, carbon particle cakes can be alternately discharged via back-washing. This eliminates the necessity for terminating the operation of the entire plant, continuous operability is enhanced, heat loss resulting from activation of the plant can be reduced, and operation costs can thus be reduced.

The reaction solution from which carbon particles had been removed is cooled to 80° C. with the second cooler 361, the pressure level is reduced to the atmospheric level with the aid of the orifice 362 and the pressure-regulating valve 363, and the resultant is transferred to the subsequent acrolein distillation apparatus. The reaction solution should be cooled to 80° C. in order to prevent expansion of the water volume when the pressure is reduced to the atmospheric level and to ensure process stability and safety.

Subsequently, the reaction solution is cooled to 50° C., which is the boiling point for acrolein, or lower, with the third cooler 364. Thus, the heating efficiency in the distillation step can be enhanced, and operation costs can be reduced. Pressure can be regulated with the use of the pressure-regulating valve 363 alone. For the purpose of reduction of a load imposed on the valve, it is preferable that the pressure-regulating valve 363 be used in combination with the orifice 362.

Figure 4:
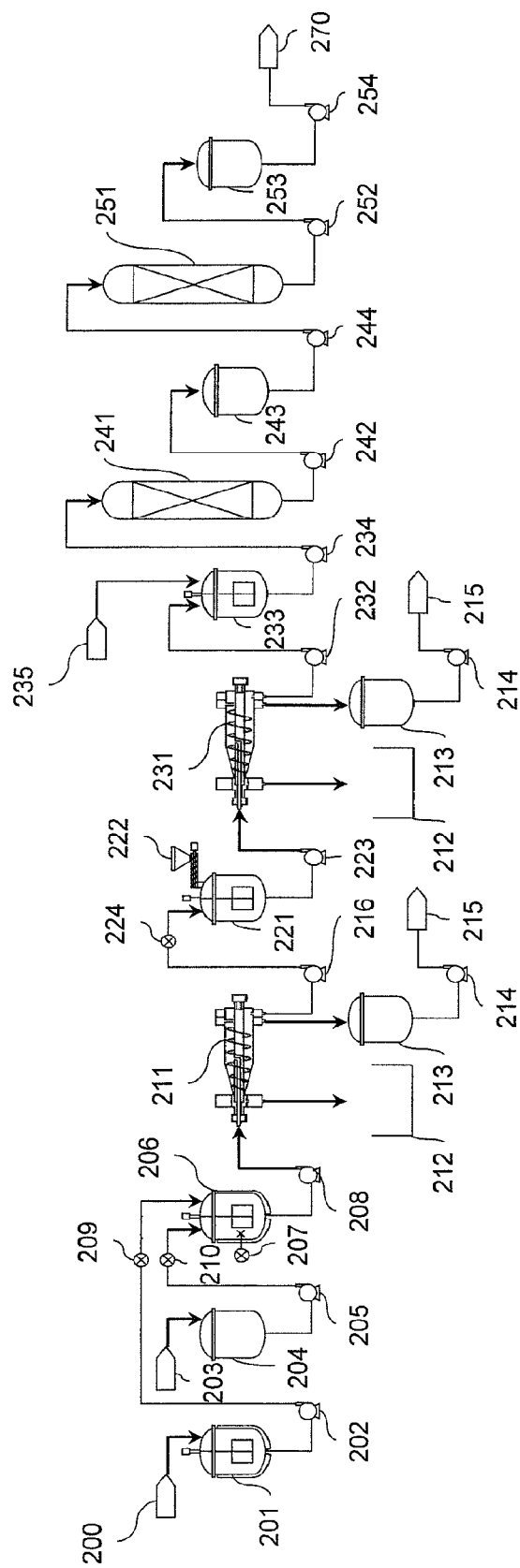
FIG. 4 shows a process for purification of a glycerin waste product.

FIG. 4 shows another embodiment of the process for purification of glycerin according to the present invention. This process further comprises a process of removing anion impurities contained in glycerin, following the process for purification of glycerin as shown in FIG. 2. Specifically, glycerin that has passed through the cation exchange tower 241 is transferred to the anion exchange tower 251, and trace amounts of anion impurities are removed. Ion-exchanged glycerin is stored in the anion-exchanged glycerin tank 253, and it is then subjected to the process 270 of supercritical water treatment. The process of allowing glycerin to pass through cation-exchange resin and the process of allowing glycerin to pass through anion-exchange resin may occasionally be carried out in the reverse order.

EXAMPLES

Hereafter, the present invention is described in greater detail with reference to the examples, although the technical scope of the present invention is not limited thereto.

Example 1

1. Preparation of Waste Glycerin

Figure 5:
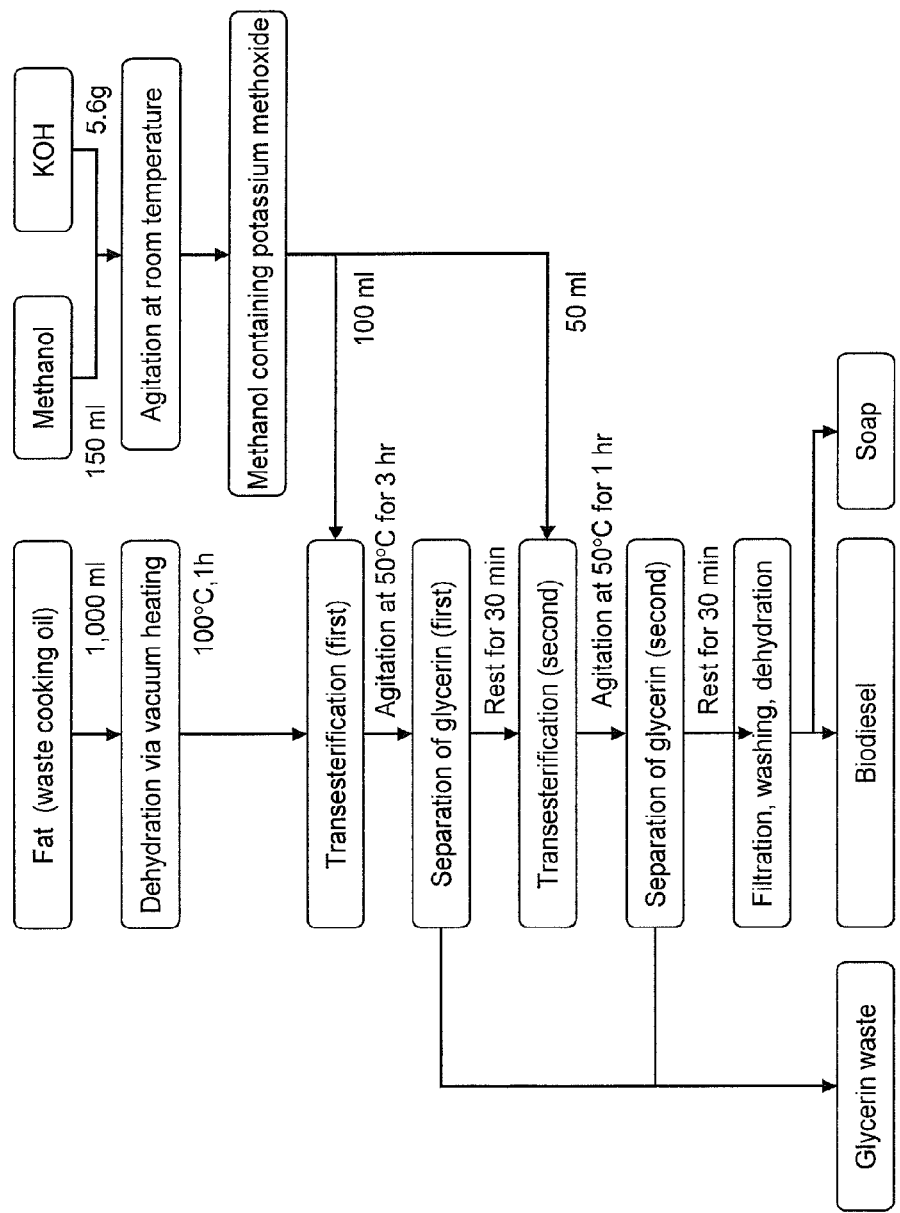
FIG. 5 is a flow diagram showing a process for biodiesel synthesis involving production of a glycerin waste product as a by-product.

An experiment of producing a glycerin waste product from waste fats as by-products was carried out. FIG. 5 shows a flow diagram showing an experiment of producing glycerin as a by-product of biodiesel synthesis. At the outset, 1,000 ml of waste cooking oil generated at a school lunch center was dehydrated via vacuum heating at 300 torr and 80° C. for 1 hour. Also, 5.6 g of potassium hydroxide was added to 150 ml of methanol with agitation at room temperature to prepare methanol containing potassium methoxide. Thus-obtained methanol containing potassium methoxide (100 ml) was added to the waste cooking oil dehydrated via vacuum heating, and the mixture was agitated at 50° C. for 3 hours to conduct the first-phase transesterification. Thereafter, the reaction solution was allowed to stand for 30 minutes, and the glycerin waste product layer as the lower layer was discharged. To the remaining waste cooking oil, 50 ml of remaining methanol containing potassium methoxide was added, and the mixture was agitated at 50° C. for 1 hour to conduct the second-phase transesterification. Thereafter, the resultant was allowed to stand for 30 minutes, and the glycerin waste product layer as the lower layer was discharged. Table 3 shows the results of component analysis of the glycerin waste products that had been collected in two separate instances. Organic matter concentration was measured via gas chromatography. Potassium concentration and magnesium concentration were quantified via ion chromatography, and moisture concentration was measured by the Karl Fischer method. Potassium is contained in an amount of 9.37% by weight in the glycerin waste product in the form of potassium sulfate. When a reaction solution with glycerin concentration of 30% by weight is to be prepared from such glycerin waste product, it is necessary that 127 g of glycerin be added relative to 100 g of water. Thus, the amount of potassium sulfate in the reaction solution is 5.24% by weight, and such amount exceeds the acceptable potassium sulfate concentration (i.e., 0.06% by weight). This may cause pipe clogging.

TABLE 3

Results of component analysis of glycerin waste product

| Components of glycerin waste product | Concentration (wt %) |
| --- | --- |
| Glycerin | 57.4 |
| Methanol | 20.7 |
| Higher fatty acid and its salt | 13.1 |
| Lower fatty acid and its salt | 0.05 |
| Potassium sulfate | 9.37 |
| Magnesium sulfate | — |
| Water | 4.5 |

2. Purification of Waste Glycerin

Figure 6:
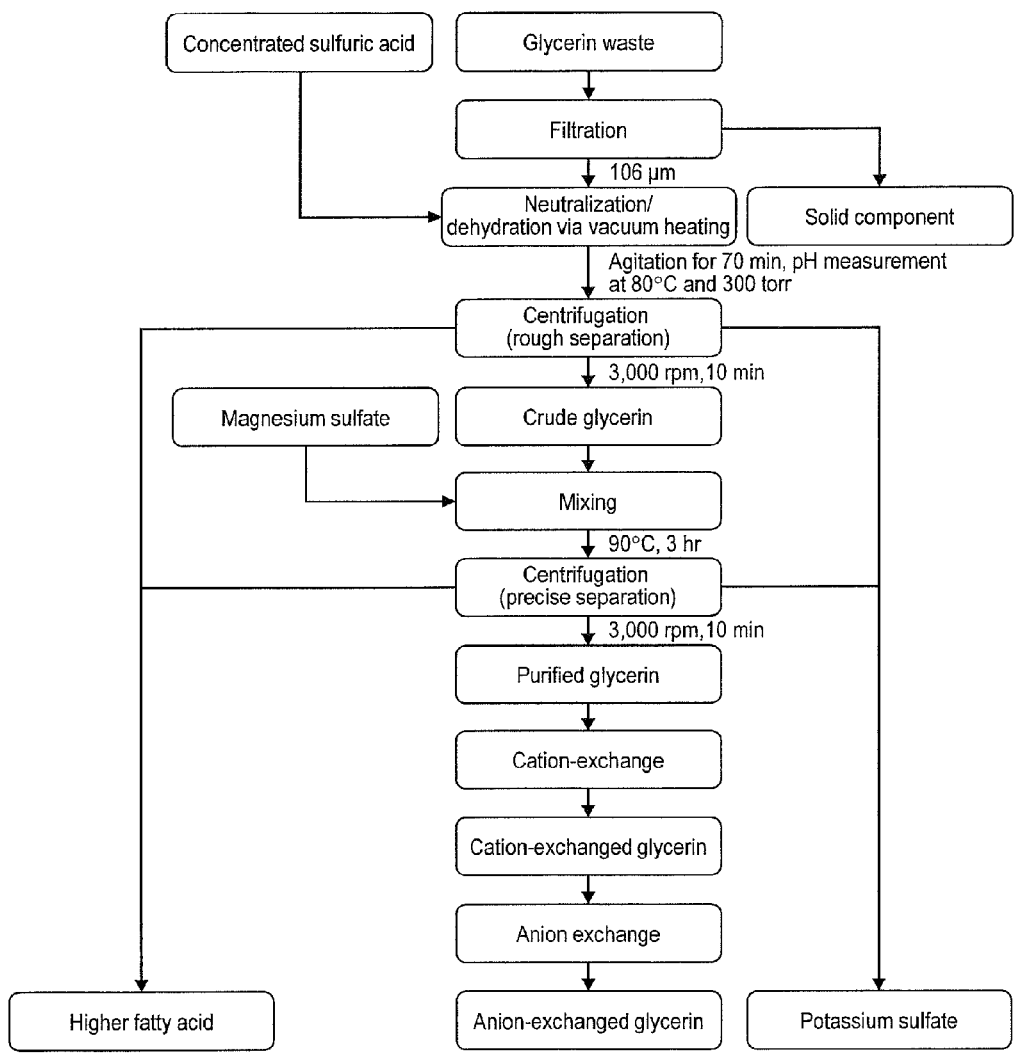
FIG. 6 is a flow diagram showing a process for purification of a glycerin waste product.
Figure 7:
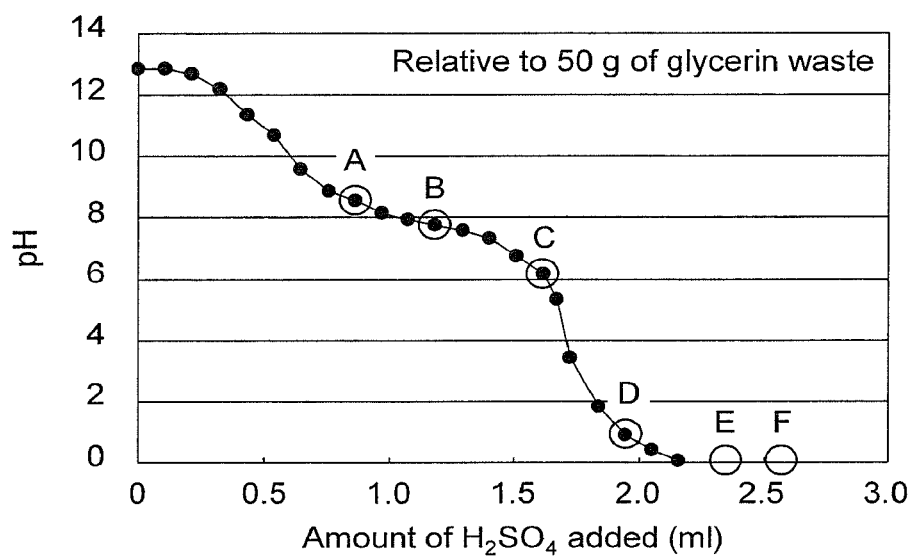
FIG. 7 is a chart showing a titration curve for the neutralization of a glycerin waste product.

An experiment of purification of a glycerin waste product was carried out. FIG. 6 shows a flow diagram of an experiment of purification of a glycerin waste product. Since waste glycerin contains solid components, solid components such as deep-fried tempura batter were removed using a sieve with a wire diameter of 71 μm and an opening of 106 μm. Subsequently, the given amount of concentrated sulfuric acid as shown in Table 4 was added to 50 g of waste glycerin, and the mixture was agitated for 10 minutes while measuring the pH level. The resultant was heated at 300 torr for 1 hour to 80° C., so as to remove methanol and water. In order to prevent inclusion of excess water, neutralization was carried out with the use of concentrated sulfuric acid instead of dilute sulfuric acid. FIG. 7 shows a titration curve attained when waste glycerin was neutralized with concentrated sulfuric acid. After the neutralized glycerin waste product had been allowed to stand for 30 minutes, the waste was separated into potassium sulfate, crude glycerin, and organic fatty acid from the lowermost layer. These components were transferred to a centrifuge tube, centrifugation was carried out at 3,000 rpm for 10 minutes, higher fatty acid as the upper layer and potassium sulfate as the lower layer were removed, and crude glycerin as the intermediate layer was collected. Table 5 shows the results of component analysis of crude glycerin. If an attention is paid to potassium ions in crude glycerin, Case B in which the pH level is at a neutral level exhibits the lowest potassium ion concentration. When a reaction solution with a glycerin concentration of 30% by weight is prepared from such crude glycerin, the potassium sulfate concentration would be 0.23% by weight in the reaction solution. That is, such concentration exceeds the acceptable potassium sulfate concentration of 0.06% by weight, and the pipe may be clogged during the process of supercritical water treatment.

In Case E and Case F, the pH level is close to 0, and glycerin concentration is the highest, although removal of sulfuric acid becomes necessary in the end. Thus, crude glycerin of Case B was selectively subjected to the desalting treatment described below.

TABLE 4

Amount of concentrated sulfuric acid added

| Case | A | B | C | D | E | F |
|---|---|---|---|---|---|---|
| Amount concentrated sulfuric acid added (g relative to 50 g of waste glycerin) | 1.47 | 2.21 | 2.94 | 3.68 | 4.23 | 4.78 |

TABLE 5

Results of component analysis of crude glycerin

| | Concentration (wt %) | | | | | |
|---|---|---|---|---|---|---|
| Components of crude glycerin | A pH = 8.54 | B pH = 7.76 | C pH = 6.15 | D pH = 0.41 | E pH < 0 | F pH < 0 |
| Glycerin | 78.9 | 81.3 | 76.8 | 76.8 | 91.0 | 89.5 |
| Methanol | 2.1 | 2.5 | 2.5 | 1.8 | 1.9 | 2.5 |
| Higher fatty acid and its salt | 10.5 | 11.0 | 15.2 | 13.9 | 0.0 | 0.0 |
| Lower fatty acid and its salt | 0.40 | 0.50 | 0.43 | 0.55 | 0.51 | 0.52 |
| Potassium sulfate | 4.50 | 0.62 | 0.89 | 3.10 | 1.90 | 2.30 |
| Magnesium sulfate | — | — | — | — | — | — |
| Water | 3.6 | 4.1 | 4.2 | 3.9 | 4.7 | 5.2 |

Figure 8:
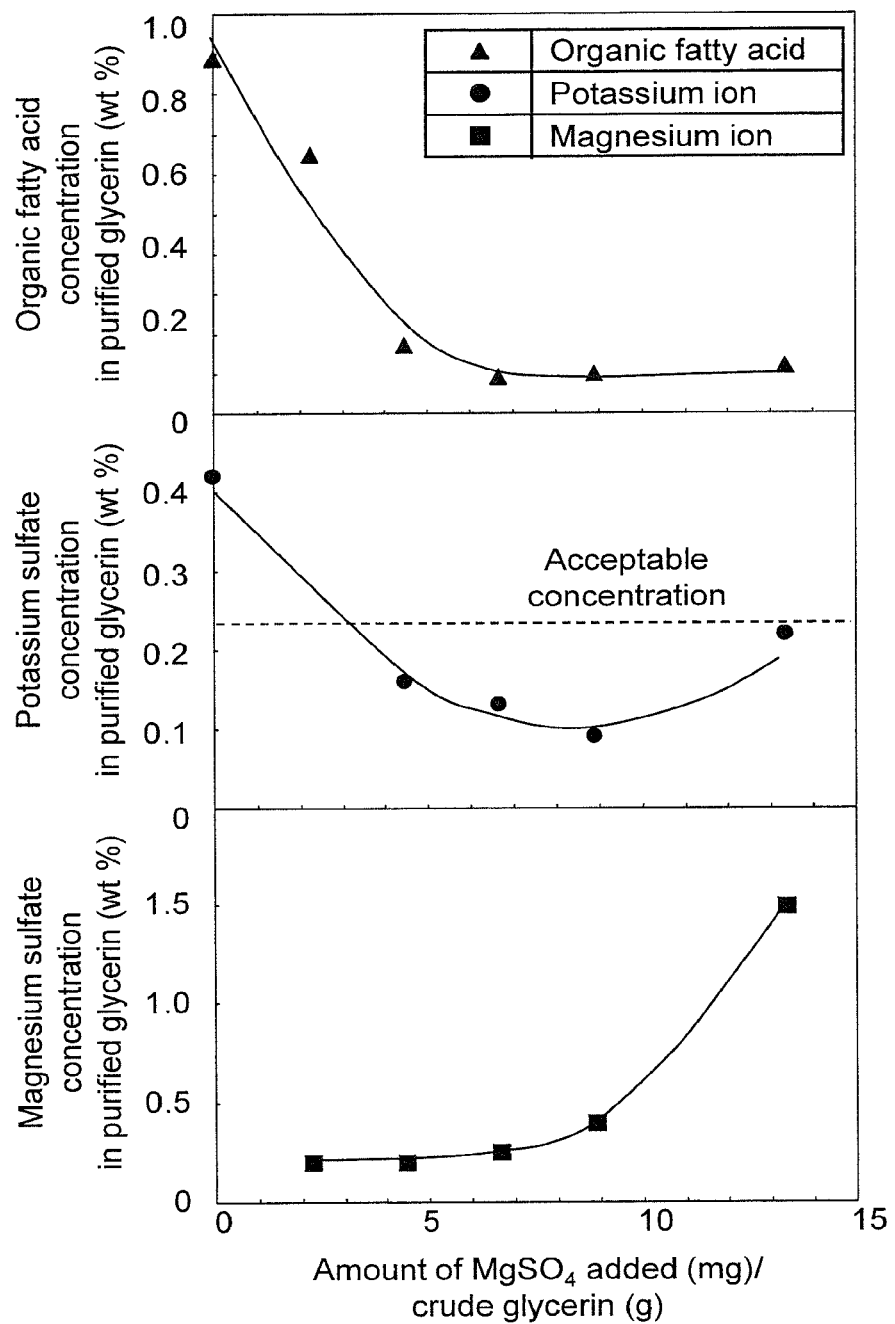
FIG. 8 is a chart showing the correlation between the amount of magnesium sulfate added and various components.

Subsequently, the given amount of magnesium sulfate shown in Table 6 was added to crude glycerin, and the mixture was agitated at 90° C. for 3 hours. Crude glycerin was subjected to centrifugation at 3,000 rpm for 10 minutes, a magnesium salt of organic fatty acid as the upper layer and potassium sulfate as the lower layer were separated and removed, and purified glycerin as the intermediate layer was collected. Table 7 and FIG. 8 show the results of component analysis of purified glycerin. When 5 mg or more magnesium sulfate was added relative to 1 g of crude glycerin, organic fatty acid concentration and potassium sulfate concentration were reduced. When purified glycerin of Case d with the lowest potassium ion concentration was used, potassium sulfate concentration was 0.03% by weight in the reaction solution with a glycerin concentration of 30% by weight, and it was possible to avoid clogging of the supercritical water pipe.

TABLE 6

Amount of magnesium sulfate added

| Case | a | b | c | d | e |
|---|---|---|---|---|---|
| Amount of magnesium sulfate added (mg relative to 1 g of crude glycerin) | 2.22 | 4.46 | 6.67 | 8.90 | 13.32 |

TABLE 7

Results of component analysis of crude glycerin

| Components of | Concentration (wt %) | | | | |
|---|---|---|---|---|---|
| crude glycerin | a | b | c | d | e |
| Glycerin | 95.1 | 99.2 | 91.8 | 90.8 | 96.4 |
| Methanol | 2.5 | 2.7 | 2.1 | 2.2 | 2.6 |
| Higher fatty acid and its salt | 2.6 | 2.7 | 2.8 | 2.6 | 2.7 |
| Lower fatty acid and its salt | 0.65 | 0.17 | 0.09 | 0.10 | 0.12 |
| Potassium sulfate | 0.56 | 0.16 | 0.13 | 0.09 | 0.22 |
| Magnesium sulfate | 0.20 | 0.20 | 0.25 | 0.40 | 1.47 |
| Water | 1.5 | 0.5 | 1.5 | 2.0 | 1.6 |

Subsequently, 10% by weight of water was added to purified glycerin to prepare a homogeneous glycerin mixture, and the resultant was subjected to desalting with the use of cation-exchange resin. Diaion PK216 (tradename, manufactured by Mitsubishi Chemical Corporation) was used as cation-exchange resin. Since the functional group of such cation-exchange resin is of a sodium type, hydrochloric acid was allowed to pass therethrough, the functional group was converted into a hydroxyl type functional group, and ion exchange was then carried out.

In the end, cation-exchanged glycerin was allowed to pass through anion-exchange resin, so as to separate and remove lower organic fatty acid. Diaion PA316 (tradename, manufactured by Mitsubishi Chemical Corporation) was used as anion-exchange resin.

Table 8 shows the results of component analysis of cation-exchanged purified glycerin and of anion-exchanged purified glycerin. Potassium sulfate and magnesium sulfate that had remained in trace amounts in purified glycerin before ion exchange were removed from cation-exchanged purified glycerin. In addition, lower fatty acids that could not be completely removed with the addition of magnesium sulfate were removed from anion-exchanged glycerin.

TABLE 8

Results of component analysis of ion-exchanged purified glycerin

|  | Cation-exchanged glycerin | Anion-exchanged glycerin |
|---|---|---|
| Glycerin | 96.4 | 97.0 |
| Methanol | 2.1 | 2.0 |
| Higher fatty acid and its salt | 0.0 | 0.0 |
| Lower fatty acid and its salt | 0.10 | 0.00 |
| Potassium sulfate | 0.00 | 0.00 |
| Magnesium sulfate | 0.00 | 0.00 |
| Water | 1.5 | 1.5 |

(unit: wt %)

3. Experiment of Supercritical Reaction

Figure 3:
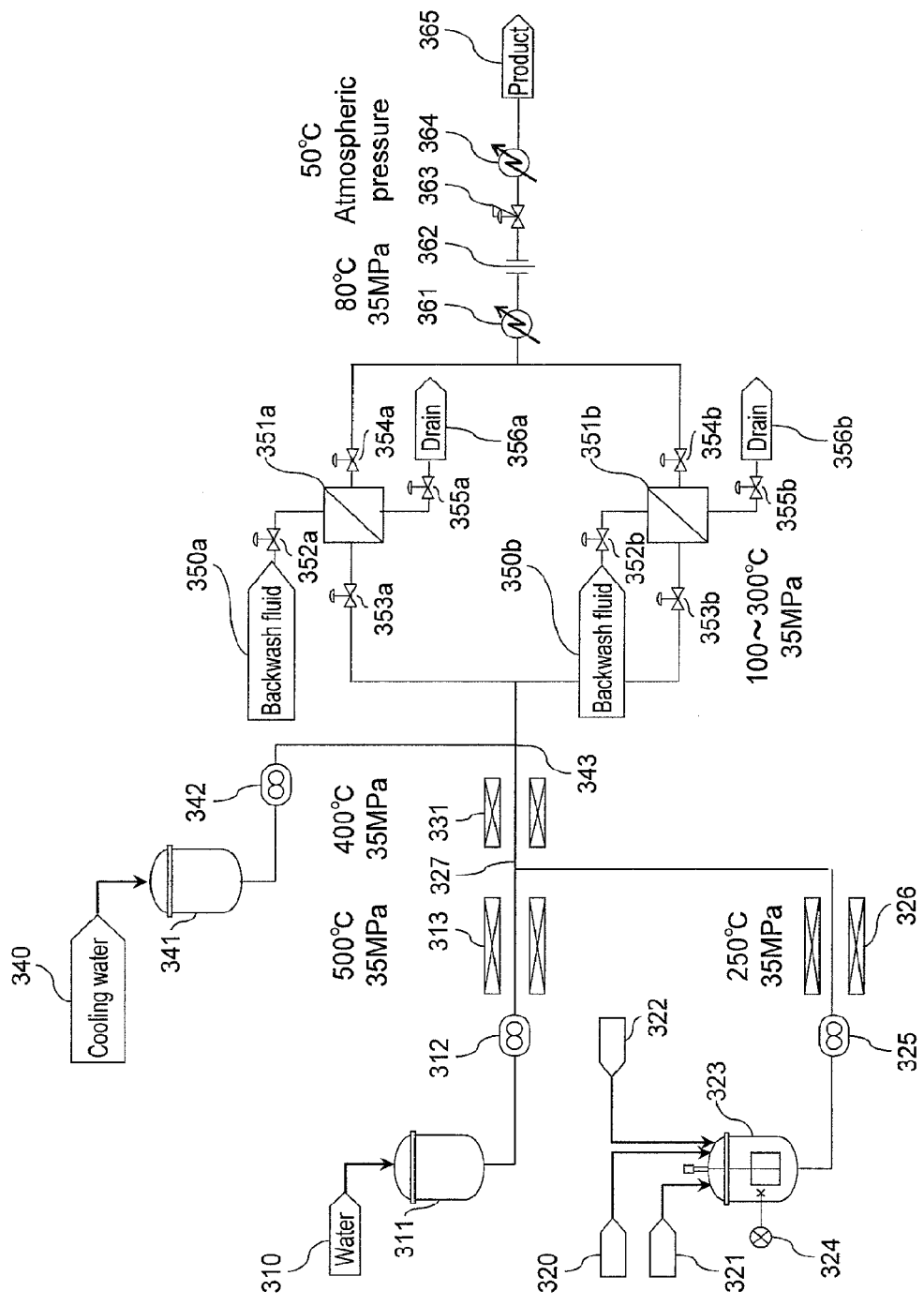
FIG. 3 shows a process of production of acrolein from purified glycerin with the use of supercritical water.

With the use of the supercritical water reaction equipment as shown in FIG. 3, subsequently, raw materials; i.e., glycerin waste products, crude glycerin, purified glycerin, cation-exchanged purified glycerin, and cation-exchanged and anion-exchanged purified glycerin, were subjected to reactions with supercritical water. As a result, clogging occurred in the supercritical water reaction pipe when the glycerin waste product with high potassium sulfate concentration and crude glycerin were used. In the case of purified glycerin from which impurities had been removed with the addition of magnesium sulfate, pressure fluctuation was observed in the supercritical water reaction tube caused by precipitation of magnesium sulfate. However, pipe clogging did not occur, and acrolein was synthesized with a reaction yield exceeding 70%. In addition, no pressure fluctuation was observed in the ion-exchanged glycerin sample, and acrolein was synthesized with a reaction yield of 70% or higher.

INDUSTRIAL APPLICABILITY

According to the method for purification of glycerin of the present invention, impurities, including alkali metals, can be removed from a glycerin waste product without the use of means such as distillation or ion exchange, which incur high operation costs. When synthesizing acrolein by allowing supercritical water and acid to react with glycerin, accordingly, clogging of a supercritical water reaction tube can be prevented. Thus, the industrial applicability of the method of the present invention is high.

All publications, patents, and patent applications cited herein are incorporated herein by reference in their entirety.

DESCRIPTION OF NUMERICAL REFERENCES

100: Methanol header
101: Methanol tank
102: Methanol pump
103: Potassium hydroxide feeder
104: Potassium methoxide production tank
105: Potassium methoxide pump
110: Fat header
111: Fat tank
112: Fat pump
113: Fat filter
114: Fat receiver tank
115: Fat pump
121: Trans esterification tank
122: Conductivity meter
123: Liquid transfer pump
124: Pre-purification BDF tank
125: Pre-purification BDF pump
126: Step of BDF purification
127: Step of glycerin purification
200: Waste glycerin header
201: Waste glycerin tank
202: Waste glycerin pump
203: Sulfuric acid header
204: Sulfuric acid tank
205: Sulfuric acid pump
206: Neutralization tank
207: pH meter
208: Neutralizer pump
209: Waste glycerin integrating flow meter
210: Concentrated sulfuric acid integrating flow meter
211: Continuous centrifuge
212: Potassium sulfate pit
213: Organic fatty acid tank
214: Organic fatty acid transfer pump
215: Step of organic fatty acid treatment
216: Crude glycerin pump
221: Magnesium sulfate mixing tank
222: Magnesium sulfate screw feeder
223: Mixture transfer pump
224: Crude glycerin flow meter
231: Continuous centrifuge
232: Purified glycerin pump
233: Purified glycerin tank
234: Purified glycerin pump
235: Water header
241: Cation exchange tower
242: Cation-exchanged glycerin pump
243: Cation-exchanged glycerin tank
244: Cation-exchanged glycerin pump
251: Anion exchange tower
252: Anion-exchanged glycerin pump
253: Anion-exchanged glycerin tank
254: Anion-exchanged glycerin pump
270: Step of supercritical water reaction
310: Water header
311: Water tank
312: Supercritical water high-pressure pump
313: Supercritical water pre-heater
320: Purified glycerin header
321: Sulfuric acid header
322: Water header
323: Raw material tank
324: pH meter
325: Raw material high-pressure pump
326: Raw material pre-heater
327: Juncture
331: Reaction tube heater
340: Cooling water header
341: Cooling water tank
342: Cooling water high-pressure pump
343: Juncture
350$a$, 350$b$: Backwashing fluid headers
351$a$, 351$b$: Filters
352$a$, 352$b$: Valves of backwashing fluid inlets of filter
353$a$, 353$b$: Valves of reaction solution inlets of filter
354$a$, 354$b$: Valves of reaction solution outlets of filter
355$a$, 355$b$: Drain valves of filter
356$a$, 356$b$: Drains
361: Cooler
362: Orifice
363: Pressure regulation valve
364: Cooler
365: Reaction solution outlet

The invention claimed is:

1. A method for purification of glycerin comprising steps of: heating glycerin containing an alkali metal, an alcohol, an organic fatty acid, and water under reduced pressure, so as to remove the alcohol and water; adding sulfuric acid to glycerin from which the alcohol and water have been removed, so as to neutralize glycerin; subjecting neutralized glycerin to centrifugation, so as to separate and remove a sulfate of alkali metal and the organic fatty acid; adding and mixing a sulfate of alkaline earth metal to glycerin collected via centrifugation; and subjecting a mixture of glycerin with the sulfate of alkaline earth metal to centrifugation, so as to separate and remove the sulfate of alkali metal and an alkaline earth metal salt of organic fatty acid.

2. A method for purification of glycerin according to claim 1, further comprising, after subjecting the mixture of glycerin with the sulfate of alkaline earth metal to centrifugation, passing the glycerin through cation-exchange resin, so as to separate and remove the alkali metal.

3. A method for purification of glycerin according to claim 2, further comprising, after passing the glycerin through cation-exchange resin, passing the glycerin through anion-exchange resin, so as to separate and remove impurities.

4. The method for purification of glycerin according to claim 1, wherein the sulfate of alkaline earth metal is magnesium sulfate.

5. The method for purification of glycerin according to claim 2, wherein the sulfate of alkaline earth metal is magnesium sulfate.

6. The method for purification of glycerin according to claim 3, wherein the sulfate of alkaline earth metal is magnesium sulfate.

* * * * *